(12) United States Patent
Balsells

(10) Patent No.: US 7,769,459 B2
(45) Date of Patent: *Aug. 3, 2010

(54) PIGTAIL SPRING CONTACTS FOR IMPLANTED MEDICAL DEVICES

(75) Inventor: Peter J. Balsells, Newport Beach, CA (US)

(73) Assignee: Bal Seal Engineering Co., Inc., Lake Forest, CA (US)

( * ) Notice: Subject to any disclaimer, the term of this patent is extended or adjusted under 35 U.S.C. 154(b) by 882 days.

This patent is subject to a terminal disclaimer.

(21) Appl. No.: 11/252,417

(22) Filed: Oct. 17, 2005

(65) Prior Publication Data

US 2006/0095086 A1 May 4, 2006

Related U.S. Application Data

(60) Provisional application No. 60/619,862, filed on Oct. 18, 2004.

(51) Int. Cl.
*A61N 1/375* (2006.01)
(52) U.S. Cl. ...................................... 607/37
(58) Field of Classification Search .................. 607/36, 607/37; 439/668, 669, 827, 909
See application file for complete search history.

(56) References Cited

U.S. PATENT DOCUMENTS 7,195,523 B2 * 3/2007 Naviaux ..................... 439/827
2004/0034393 A1 * 2/2004 Hansen et al. ................ 607/37

OTHER PUBLICATIONS

MMXpress; Hodges, Jason; Connection options—12 Volt Electrical Connections; Apr. 6, 2002; pp. 1-3.*

* cited by examiner

*Primary Examiner*—George R Evanisko
*Assistant Examiner*—Michael D'Abreu
(74) *Attorney, Agent, or Firm*—Walter A. Hackler

(57) ABSTRACT

Spring contact apparatus for an implantable medical device includes a plurality of nonconductive housing with each housing having a bore therethrough alignable with adjacent housing bores and assembled in spaced apart pairs with adjacent radial accesses to adjacent housing chambers. A plurality of electrically conductive garter springs are provided with the pairs of garter springs being disposed in corresponding adjacent housing chambers and each spring having a pigtail lead extending through a corresponding axis. The pairs of adjacent pigtail leads extending from adjacent axes are of sufficient length for a combined attachment to a corresponding pulse generator lead.

1 Claim, 2 Drawing Sheets

Fig. 1.
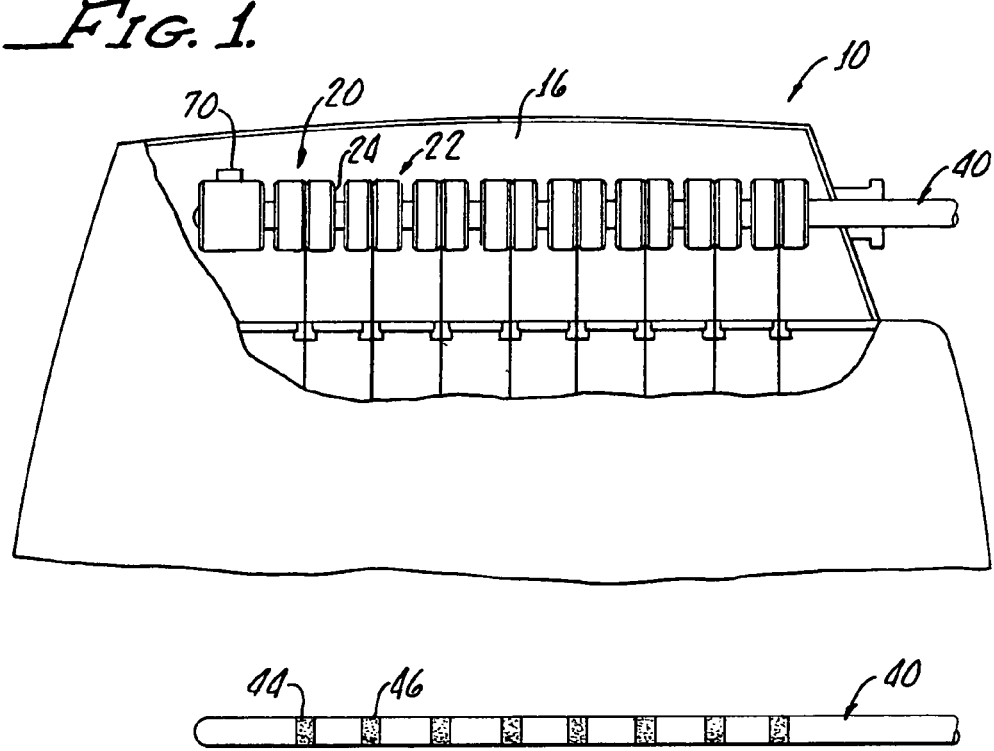
Fig. 2.
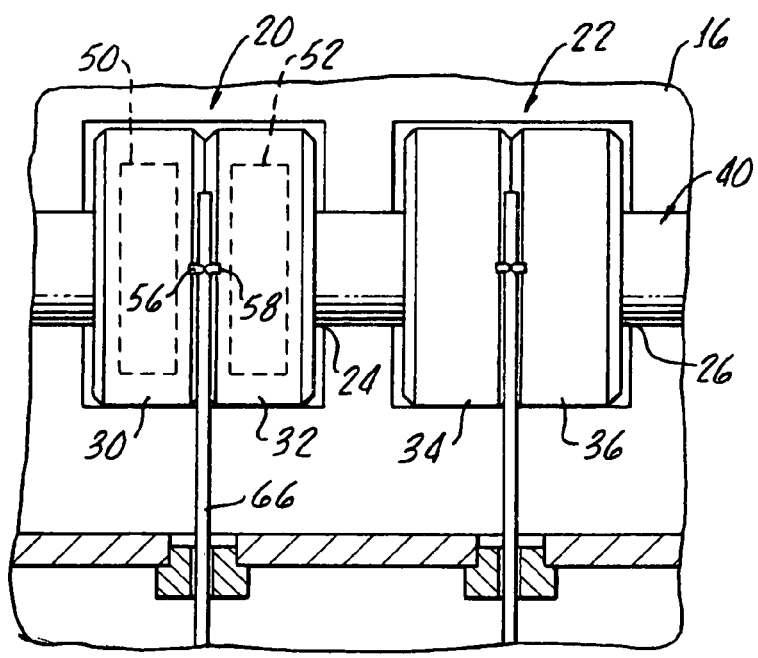
Fig. 3.

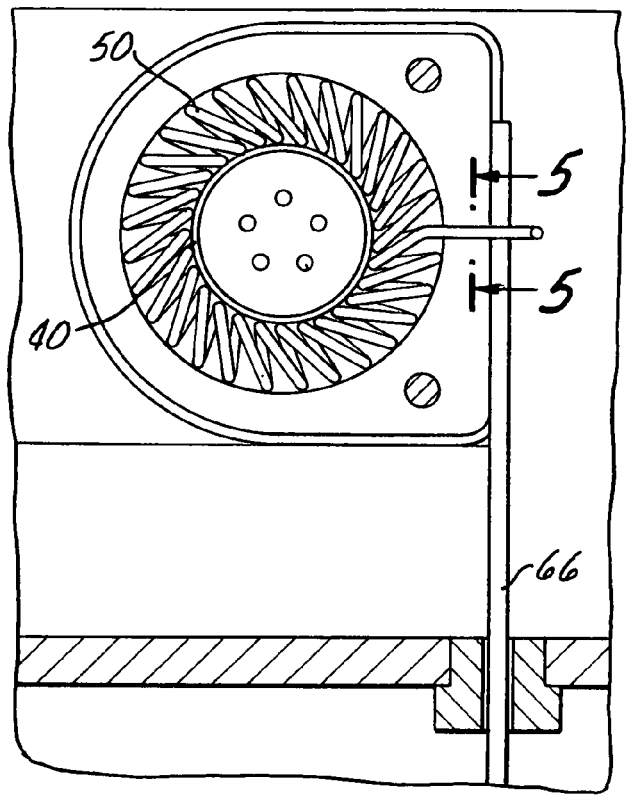
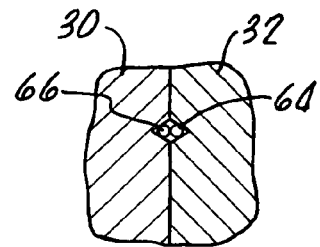
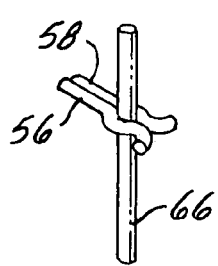
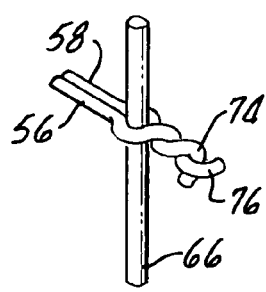
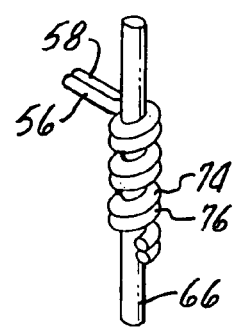
Fig. 4.
Fig. 5.
Fig. 6.
Fig. 7.
Fig. 8.

PIGTAIL SPRING CONTACTS FOR IMPLANTED MEDICAL DEVICES

The present application claims priority from U.S. Ser. No. 60/619,862 filed on Oct. 18, 2004, which is incorporated herewith in its entirety by this subject reference thereto.

This invention is generally directed to implantable medical devices and is more particularly directed to the electrical conductive path between a pulse generator and the implantable lead or leads.

Implantable medical electronics devices consist of an implanted pulse generator that is used to provide electrical stimulation to certain tissues and an implantable lead or leads that are used to transmit the electrical impulse to the targeted tissues. The first ones were developed for cardiac pacemaking, and that area now has a number of applications for cardiac rhythm management, treatments for congestive heart failure, and implanted defibrillators. Other devices are used for neurostimulation with a wide range of uses such as pain control, nervous tremor mitigation, incontinent treatment, epilepsy seizure reduction, vagus nerve stimulation for clinical depression and others. This rapidly growing field will undoubtedly have even wider application in the future.

In general, the devices consist of an implanted pulse generator that may also be capable of sensing body activity such as an irregular heartbeat. The pulse generator generates an electrical pulse or signal that is transmitted to a targeted tissue or tissues or nerve area or areas through an implanted lead. Once the leads are implanted in the body, removal may involve major surgery with an attendant risk factor. Therefore, a reliable method of connecting and disconnecting the leads is required since the implanted pulse generator may have to be replaced to update the unit or to replace the battery.

The unit is a hermetically sealed enclosure containing the circuitry and a power supply. Current practice is to place a molded header containing a connector on top of the unit to provide a means of housing the electrical contacts for the leads. While some applications are very simple requiring only two leads because they only have to transmit two discrete signals to the tissues, others are very complex and require a very large number of discrete electrical impulses. Each electrical impulse then requires a discrete conductive path between the impulse generator and the implanted lead.

Several different types of contacts are in use ranging from setscrews to various types of spring contacts. These contacts are embedded in the connector which is generally made of a silicon filled implantable polymeric. The lead generally consists of a series of conductive rings separated by insulative spaces so that when it is fully inserted into the header, each contact ring is placed in contact with the connector contact. Each contact in turn has to be connected to a discrete lead from the pulse generator.

In current practice, the connector generally consists of a setscrew in a metal connector or some type of spring in a metal housing. Where the spring is used, it provides the conductive path between the metal housing and the contact ring of the lead. Setscrews are very undesirable where large numbers of connectors are required because each connector must be tightened with a torque wrench. A spring retained in a metal housing provides a reliable contact with controlled insertion forces that is convenient for both insertion and removal obviates the requirement for a torque wrench. A canted coil spring has very desirable characteristics for this application since its nearly constant force over a wide range of deflection compensates for any irregularities on the surface of the lead electrical contact rings and the insertion force can be controlled.

The housings, which can number anywhere from two to twenty-four or even more are now machined from metals such as MP35N, titanium, or even platinum, are significant cost drivers. The present invention utilizes an implantable polymeric biocompatible material housing that can be fabricated by injection molding to reduce the cost of the contacts with an electrical path.

SUMMARY OF THE INVENTION

Spring contact apparatus in accordance with the present invention for implanted medical devices generally includes a plurality of nonconductive housings each having a bore therethrough alignable with adjacent housing bores and assembled in a spaced apart relationship with adjacent radial accesses to adjacent housing chambers.

A plurality of electrical conductive garter springs is provided with pairs of garter springs being disposed in corresponding adjacent housing chambers. Each spring includes a pigtail lead which extends through a corresponding access with the pairs of springs having adjacent pigtail leads which extend from adjacent accesses with sufficient length for combined attachment to a corresponding pulse generator lead.

The apparatus in accordance with the present invention may further include a header and the nonconductive housings are assembled in the spaced apart pair relationship within the header.

In one embodiment of the present invention, corresponding pulse generator leads are snap fitted between corresponding adjacent pigtail leads.

In another embodiment of the present invention, corresponding pulse generator leads are attached to corresponding adjacent piglet leads by twisting of the adjacent pigtail leads.

In further embodiment of the present invention, the corresponding pulse generator leads are attached to the corresponding adjacent pigtail leads by welding.

Still another embodiment in accordance with the present invention provides for attachment of the pulse generator leads to the corresponding adjacent pigtail leads by wrapping of the adjacent pigtail leads about the corresponding pulse generator lead.

BRIEF DESCRIPTION OF THE DRAWINGS

The present invention may be more clearly appreciated when taken in conjunction with the accompanying drawings in which:

FIG. 1 is a plan view of spring contact apparatus in accordance with the present invention having a header partially broken away to show a plurality of nonconductive spaced apart housings along with a plurality of corresponding pulse generator leads and rod receiving housing bores for effecting electrical communication between spaced apart electrical terminals on the rod and spaced apart spring pairs, as hereinafter described in greater detail;

FIG. 2 is a plan view of the rod shown in FIG. 1, more specifically illustrating a plurality of spaced apart electrical terminals thereon;

FIG. 3 is an enlarged view of nonconductive housings assembled in spaced apart pairs;

FIG. 4 is a cross sectional view of one of the housings illustrating a spring position therein having a pigtail lead extending through an access through the housing;

FIG. 5 is a sectional view taken along the line 5-5 of FIG. 4 illustrating adjacent housing accesses through which adjacent pigtails may extend;

FIG. 6 illustrates a snap fitting between corresponding adjacent pigtail leads and a pulse generator leads;

FIG. 7 illustrates a twist attachment of adjacent pigtail leads around a generator lead; and FIG. 8 illustrates adjacent pigtail leads fixed to a corresponding pulse generator lead by wrapping of adjacent pigtail leads.

DETAILED DESCRIPTION

With reference to FIG. 1, there is shown spring contact apparatus 10 for an implantable medical device 12 which includes a header 16 along with a plurality of nonconductive housings 20, 22 each having a bores 24, 26 therethrough.

The housings 20, 22 are assembled in spaced apart pairs 30, 32 and 34, 36. A rod 40 is receivable by the housing bores 24, 26 and, as more clearly shown in FIG. 2, includes a plurality of spaced apart electrical terminals 44, 46 corresponding to the spaced apart housing pairs 20, 22.

With reference to FIGS. 3-5, a plurality of electrically conductive garter springs 50 are disposed in corresponding adjacent housing chambers 30, 32, 34, 36 with each spring 50, 52 including adjacent pigtail leads 56, 58 extending from adjacent axes 62, 64 of the housings 30, 32 with sufficient length to enable combined attachment to a corresponding pulse generator lead 66.

Shown assembled in FIG. 1, with the rod 40 in position for maintaining electrical contact between the springs 50, 52 and terminals 44, 46, a conventional latch 70 range may be provided for securing the rod 40 within the housings 20, 22.

Materials of construction of the present invention are conventional and of any type suitable for use in the medical implants. In addition, while a plurality of housings springs are illustrated in the figures, only a limited number are identified herewith by character references in order to simplify the description. It should be appreciated that all the spaced apart elements, including the housings 20, 22, springs 50, 52, pigtail leads 56, 58, impulse generator lead 60 are identical in construction.

The paired springs 50, 52 in adjacent housings 20, 22 are provided to insure electrical contact between the terminals 44, 46 and springs 50, 52. Further, the adjacent nature of the springs 50, 52 and particularly the adjacent positioning of pigtail leads 56, 58 facilitates and enhances coupling between the pulse generator leads 66 and the springs 50, 52.

A number of different structures may be utilized for implementing the electrical connection between the adjacent pigtail leads 56, 58 and the pulse generator lead 66.

For example, in FIG. 3, the pigtail leads 56, 58 are welded to the pulse generator lead 66.

Alternative connections are illustrated in FIGS. 6, 7, and 8. As illustrated in FIG. 6, the pulse generator lead 66 is snap fitted between corresponding adjacent pigtail leads 56, 58. In FIG. 7, the pigtail leads 56, 58 are connected to the pulse generator lead by twisting 74, 76 of corresponding adjacent pigtail leads 56, 58.

In FIG. 8, attachment between the pigtail leads 56, 58 and the pulse generator lead 66 is accomplished through wrapping of the ends 74, 76 about the pulse generator lead 66.

Although there has been hereinabove described a specific pigtail spring contacts for implanted medical devices in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. Spring contact apparatus for an implantable medical device, the apparatus comprising:
   a header;
   a plurality of electrically non-conductive housings, each housing having a chamber and a bore therethrough alignable with adjacent housing bores and assembled in spaced apart abutting pairs within the header with adjacent radial accesses to adjacent housing chambers;
   a plurality of electrically conductive garter springs, with pairs of the garter springs being disposed in adjacent housing chambers; and
   a plurality of pigtail leads, wherein each pigtail lead is connected to a said garter spring, wherein adjacent pigtail leads are mechanically and electrically connected together and interconnect corresponding pairs of garter springs and extend through a corresponding access, with sufficient length for attachment to a pulse generator; and
   a rod receivable by the housing bores, said rod having a plurality of spaced apart electrical terminals corresponding to the spaced apart spring pairs.

* * * * *